US012071399B2

(12) United States Patent
Hiltunen et al.

(10) Patent No.: US 12,071,399 B2
(45) Date of Patent: Aug. 27, 2024

(54) PROCESS FOR THE PREPARATION OF ARYLSULFONYLPROPENENITRILES

(71) Applicant: Kemira Oyj, Helsinki (FI)

(72) Inventors: Jaakko Hiltunen, Kauniainen (FI); Petteri Suominen, Espoo (FI); Ivan Ogibalov, Tartu (EE); Ain Uustare, Tartu (EE)

(73) Assignee: Kemira Oyj, Helsinki (FI)

( * ) Notice: Subject to any disclaimer, the term of this patent is extended or adjusted under 35 U.S.C. 154(b) by 457 days.

(21) Appl. No.: 17/290,889

(22) PCT Filed: Nov. 4, 2019

(86) PCT No.: PCT/FI2019/050780
§ 371 (c)(1),
(2) Date: May 3, 2021

(87) PCT Pub. No.: WO2020/094917
PCT Pub. Date: May 14, 2020

(65) Prior Publication Data
US 2022/0002241 A1 Jan. 6, 2022

(30) Foreign Application Priority Data

Nov. 5, 2018 (FI) .................................. 20185934

(51) Int. Cl.
*C07C 315/04* (2006.01)
*C07C 317/32* (2006.01)
(52) U.S. Cl.
CPC .......... *C07C 315/04* (2013.01); *C07C 317/32* (2013.01)
(58) Field of Classification Search
CPC .................................................. C07C 315/04
See application file for complete search history.

(56) References Cited

U.S. PATENT DOCUMENTS

| 3,541,119 A | 11/1970 | Richter et al. |
| 4,049,695 A | 9/1977 | Burk et al. |
| 10,919,847 B2 * | 2/2021 | Aaltonen .............. C07C 315/04 |

FOREIGN PATENT DOCUMENTS

| CN | 111108095 A | 5/2020 |
| JP | 2011231045 A | 11/2011 |

OTHER PUBLICATIONS

Search Report and English Translation thereof issued in corresponding CN application No. 2019800753308 on Jan. 12, 2023, 7 pages.
C. M. M. da Silva Corrêa et al., Reactions of the free toluene-p-sulphonyl radical. Part I. Diagnostic reactions of free radicals, Journal of the Chemical Society C: Organic, pp. 1874-1879, Issue 0 (1968)—Abstract Only.
International Search Report and Written Opinion for Intenrational Application No. PCT/FI2019/050780 mailed on Jan. 22, 2020.
Tassaporn Sawangphon et al.: "An Improved Synthesis of Vinyl-and [beta]-Iodovinyl Sulfones by a Molecular Iodine-Mediated One-Pot Iodosulfonation-Dehydroiodination Reaction", Synthetic Communications, vol. 43, No. 12, Jun. 18, 2013, pp. 1692-1707.
Ermolaeva, V.V. et al. Synthesis and reactions of alpha, beta-unsaturated sulfones. In: Izvestiya Vysshikh Uchebnykh Zavedenii, Khimya i Khimicheskaya Tekhnologiya 2003, vol. 46, No. 9, 9-10, Russian,compound IV, Scheme 1.
Asscher, M. et al. Chlorine-activation by redox-transfer. Part IV. The addition of sulphonyl chlorides to vinylic monomers and other olefins. In: Journal of the Chemical Society 1964, pp. 4962-4971.
Search Report for Finnish Application No. 20185934 dated Aug. 14, 2019.

* cited by examiner

Primary Examiner — Golam M Shameem
(74) Attorney, Agent, or Firm — Meunier Carlin & Curfman LLC

(57) ABSTRACT

The present invention relates to a process for the preparation of arylsulfonylpro-penenitriles. The reaction starting from arylsulfonyl halides is catalyzed by a cat-alyst compound comprising a transition metal. The process is scalable, environ-mentally benign and provides the product in good yield.

20 Claims, 1 Drawing Sheet

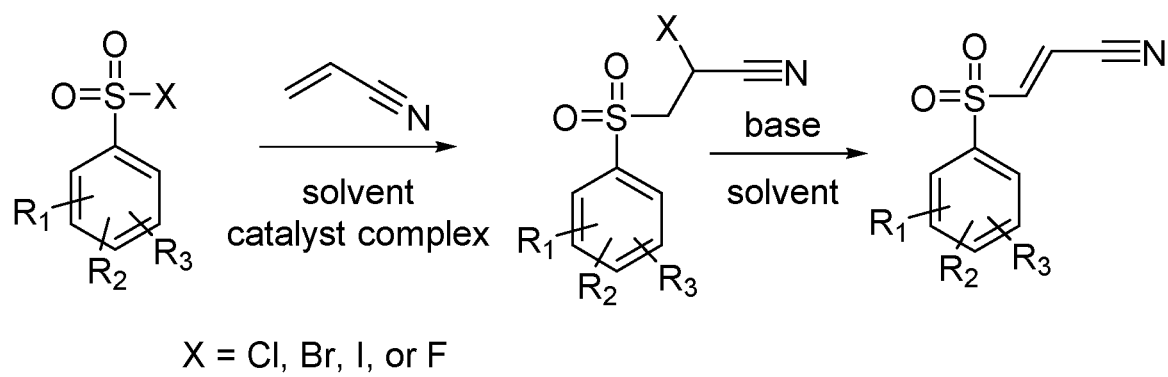

PROCESS FOR THE PREPARATION OF ARYLSULFONYLPROPENENITRILES

PRIORITY

This is a U.S. national stage application of the international application number PCT/FI2019/050780 filed on Nov. 4, 2019, and claiming priority of FI 20185934 filed on Nov. 5, 2018, the contents of both of which are incorporated herein by reference.

The present invention relates to a process for the preparation of arylsulfonylpropenenitriles by catalyzed reactions from arylsulfonyl halides. The process reduces the amount of harmful chemicals required as well as reducing the amount of chemical waste produced in order to facilitate a more environmentally benign manufacturing process for this class of compounds, is scalable and gives the products in good yields.

BACKGROUND

Compounds incorporating a vinylarenesulfonyl moiety have been found to be biologically interesting as potential neuroprotective agents against Parkinson's Disease, as antitrypanosomal agents against African sleeping sickness and as a means to combat *Staphylococcus aureus* by inhibition of a sortase SrtA isoform, just to name a few. Synthetically vinylarenesulfonyls are interesting due to their capability to act as Michael acceptors and due to their variety of cycloaddition reactions.

The applicant has also recently submitted an application disclosing several uses arylsulfonylpropenenitriles as biocides further adding to the interest in robust methods for the large-scale synthesis of compounds of this type.

The known synthesis methods for these compounds generally suffer from one or more drawbacks limiting their utility in the large-scale synthesis of the desired compounds. Among these drawbacks are low reactivity leading to poor yields and extended reaction times, expensive starting materials, complicated isolation procedures, and toxic, volatile, and/or flammable solvents used.

In order to make it possible to further explore the usefulness of the arylsulfonylpropenenitriles in many fields of application there is a need for a simple and cost-effective yet environmentally benign method suitable for the large-scale synthesis of these compounds.

SUMMARY OF THE INVENTION

It was surprisingly found that arylsulfonylpropenenitriles can be readily synthesized from inexpensive sulfinates using a reaction with a suitable vinylic compound such as acrylonitrile in the presence of a suitable catalyst. The use of a suitable and efficient catalyst to drive the conversion in the reaction enables the use of smaller amount of reactants and shorter reaction times leading to significant savings in cost in the form of reduced waste and energy requirement.

One aspect of the present invention is a process for the preparation of a compound according to general formula (I) from an arylsulfonylhalide by a catalyzed reaction with a suitable alkene wherein $R_1$, $R_2$ and $R_3$ independently represent a hydrogen atom; halogen atom; hydroxy group; amino group; alkylamino group; alkyl group; hydroxyalkyl group; haloalkyl group or alkoxy group having 1 to 4 carbon atoms; or an acylamido group having 1 to 10 carbon atoms. The intermediate formed in the reaction undergoes base-catalyzed elimination of a halide to afford the target compound in good yields. The R-groups of the target compound can be varied according to the desired use of said compound(s).

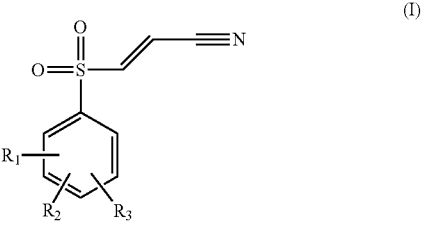

BRIEF DESCRIPTION OF FIGURES

FIG. 1 presents a scheme of the reaction used for the synthesis of the arylsulfonylpropenenitriles.

DETAILED DESCRIPTION

As used herein, the term "catalyst complex" is used to describe a combination of individual atoms, groups of atoms, or molecules that have a total net charge of zero that is able to catalyze a chemical reaction. The catalyst complex itself comprises a central atom, group of atoms, or molecule as well as a ligand. A non-limiting example of such a catalyst complex is the copper iodide triethylamine hydrochloride-complex (CuI—HCl*TEA).

A method for the preparation of arylsulfonylpropenenitriles is described herein. The method accomplishes the rapid conversion of the arylsulfonylhalide used as starting material to the desired arylsulfonylpropenenitrile. Optionally, the arylsulfonylhalide used in the reaction is synthesized separately or generated in situ. It has been surprisingly found that the reaction speed and conversion is greatly enhanced by the use of an efficient catalyst complex comprising a metal halide and the salt of an organic compound.

Previously reported syntheses of vinylarenesulfonyl compounds all suffer from various drawbacks that limit the utility of these methods when scaling production to industrial scale.

One major problem arises from the use of solvents that are either banned from or not recommended for use for a number of reasons. The solvents used in previously published syntheses of vinylarenesulfonyl compounds include dichloromethane (environmentally harmful, volatile), diethyl ether (harmful, forms explosive peroxides, volatile, extremely flammable), N,N-dimethylformamide (toxic), ethyl acetate (harmful, volatile, flammable), and acetonitrile (slightly toxic, volatile, intermittent problems with availability, flammable, expensive), as well as neat conditions wherein the acrylonitrile also acts as the solvent.

In some cases, some of the starting materials used in known methods are either not available commercially in bulk and/or laboratory scale or are too expensive to make their use practical. Thus, there was a need to develop a simple, economical, scalable, and environmentally benign method for the synthesis of vinylarenesulfonyl compounds.

In the present disclosure, we show that it is possible to efficiently synthesize arylsulfonylpropenenitriles of formula (I) from the corresponding halides using a catalyzed reaction. Compared to the traditional synthetic methods this leads to a short reaction time, good conversions, an improved impurity profile, and the ability to use environmentally benign solvents.

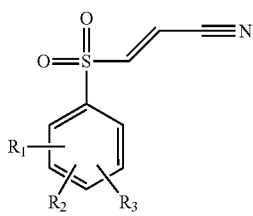

(I)

In one embodiment of the invention, $R_1$, $R_2$, and $R_3$ independently represent a hydrogen atom; a halogen atom; a hydroxy group; an amino group; an alkylamino group having 1 to 4 carbon atoms; an alkyl group having 1 to 4 carbon atoms; a hydroxyalkyl group having 1 to 4 carbon atoms; a haloalkyl group having 1 to 4 carbon atoms, or an alkoxy group having 1 to 4 carbon atoms; or an acylamido group having 1 to 10 carbon atoms.

In another embodiment of the invention, $R_1$ represents a methyl group; an ethyl group, a propyl group; a butyl group; a methoxy group; an ethoxy group; a propoxy group; an isopropoxy group; a n-butoxy group; or a tertiary butoxy group; and $R_2$ and $R_3$ represent independently a hydrogen atom; a methyl group; an ethyl group, a propyl group; a butyl group; a methoxy group; an ethoxy group; a propoxy group; an isopropoxy group; a n-butoxy group; a tertiary butoxy group.

In a preferred embodiment of this invention $R_1$ represents a methyl group in the 4-position and $R_2$ and $R_3$ both represent hydrogen as presented in formula (II).

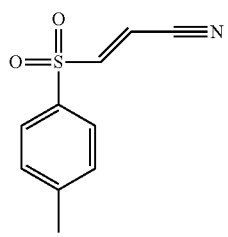

(II)

In one embodiment of the invention the organic solvent used is selected from the group containing sulfolane, 1,4-dioxane, ethyl acetate, acetone, propylene carbonate, acetonitrile or 2-methyltetrahydrofuran, dichloromethane, trichloromethane, carbon tetrachloride, toluene, xylenes, unsymmertrical ethers, polyethyleneglycols, or any mixture thereof. In another embodiment, the organic solvent used is acetonitrile, sulfolane, 1,4-dioxane, or any mixture thereof, preferably sulfolane.

In one embodiment of the present invention, the sulfonyl halide is an iodide, bromide, chloride, fluoride, or a mixture thereof, preferably a chloride.

In another embodiment of this invention, water is added to the organic solvent in an amount that is 0.1 to 20% (V/V), preferably 3 to 10% (V/V), most preferably 5% (V/V) to further enhance the reaction speed and conversion.

In yet another embodiment of this invention, the amount of water contained in the organic solvent during the reaction is less than 50% (V/V), less than 20% (V/V), less than 15% (V/V), less than 10% (V/V), less than 5% (V/V), less than 2% (V/V), less than 1% (V/V), less than 0.5% (V/V), less than 0.2% (V/V), less than 0.1% (V/V) or 0% (V/V).

In still another embodiment of this invention, the amount of water contained in the organic solvent during the reaction is more than 50% (V/V), more than 20% (V/V), more than 15% (V/V), more than 10% (V/V), more than 5% (V/V), more than 2% (V/V), more than 1% (V/V), more than 0.5% (V/V), more than 0.2% (V/V), or more than 0.1% (V/V).

In one embodiment of the present invention, the catalyst complex comprises an inorganic halide and a salt of an organic compound.

In one embodiment of the present invention, the inorganic halide is a metal halide, preferably a transition metal halide, more preferably a copper halide.

In one embodiment of the present invention, the catalyst complex comprises a copper halide selected from the group containing copper iodide, copper bromide, copper fluoride, copper chloride, or a mixture thereof. In one embodiment the catalyst complex comprises copper iodide, copper chloride, or a mixture thereof.

In one embodiment of the present invention, the copper halide may be a halide salt of Cu(I) or Cu(II).

In one embodiment of the invention, the copper and halide components of the copper halide may be added separately. In a specific embodiment of the invention, the copper ions are added as copper chloride, copper bromide, copper iodide, or any mixture thereof. In a further specific embodiment, the halide is added as any suitable organic or inorganic halide salt, preferably potassium halide, sodium halide, lithium halide, tetramethyl ammonium halide, tetraethyl ammonium halide, or any mixture thereof, more preferably potassium iodide, sodium iodide, lithium iodide, tetramethyl ammonium iodide, tetraethyl ammonium iodide, or any mixture thereof.

In one embodiment of the present invention, the salt is the salt of an acid and a base, preferably the salt of an organic base and inorganic acid, more preferably the salt of an amine and an inorganic acid, most preferably triethylamine hydrochloride.

In one embodiment of the present invention, all of the starting materials are added to the reaction vessel in one portion.

In one embodiment of the present invention, the acrylonitrile is added in one portion to a stirred solution of sulfonyl halide and catalyst complex in a solvent. In another embodiment of the present invention, the acrylonitrile is added to a stirred solution of sulfonyl halide and catalyst complex in a solvent in two portions. In yet another embodiment of the present invention, the acrylonitrile is added to a stirred solution of sulfonyl halide and catalyst complex in a solvent in at least three portions.

In a specific embodiment, the acrylonitrile is added to the reaction mixture as a continuous addition.

In a specific embodiment of the present invention, the catalyst complex comprises copper chloride, copper iodide, or a mixture thereof and triethylamine hydrochloride. In a very specific embodiment of the present invention, the catalyst complex comprises copper iodide and triethylamine hydrochloride.

In one embodiment of the present invention, the catalyst complex comprises a molar excess of organic salt in relation to the inorganic halide. In specific embodiments of the present invention, the catalyst complex comprises 5 or less, 3 or less, 2 or less, or 1.5 or less equivalents of organic salt relative to the molar amount of inorganic halide.

In one embodiment of the present invention, the amount of catalyst complex added to the reaction mixture is less than 30 mol-%, less than 15 mol-%, or 10 mol-% of catalyst complex relative to the amount of the sulfonyl halide.

In one embodiment of the present invention, the amount of catalyst complex added to the reaction mixture is at least 5%, at least 2%, at least 1%, at least 0.5%, or at least 0.1% relative to the amount of the sulfonyl halide.

In one embodiment of this invention, the amount of acrylonitrile (in mol) used relative to the amount of sulfonyl halide is less than 5 equivalents, less than 4 equivalents, less than 3 equivalents, less than 2 equivalents, less than 1.5 equivalents, less than 1.2 equivalents or 1 equivalent.

In another embodiment of this invention, the amount of acrylonitrile (in mol) used relative to the amount of sulfonyl halide is at least 1 equivalent, at least 1.1 equivalents, at least 1.2 equivalents, at least 1.5 equivalents, at least 2 equivalents, or at least 3 equivalents.

The present invention enables completing the reaction with short reaction times. In one embodiment of the present invention the reaction time required for the formation of the arylsulfonylpropenenitriles compounds is less than 24 hours, preferably less than 12 hours, most preferably 8 hours or less.

The present invention enables completing the reaction at low reaction temperatures. In one embodiment of the present invention the reaction is performed at a temperature of 200° C. or less, 175° C. or less, preferably 150° C. or less, most preferably 125° C. or less.

In one embodiment of the present invention, the reaction temperature is more than 75° C., more than 50° C., or more than 20° C.

It will be clear to a person skilled in the art that the selection of the temperature at which the reaction is run will also be influenced by technical aspects such as the type of reactor used. As a non-limiting example, it is noted that the relatively low boiling point of acrylonitrile (77° C.) imposes limitations on the temperature at which the reaction can be performed using a reactor open to the atmosphere. Optimization of the temperature is considered to be a task to be routinely performed by one skilled in the art.

In a specific embodiment of the present invention, the reaction may be heated by any means known to a person skilled in the art. Non-limiting examples of modes of heating that may be used include thermal heating using an oil-bath, a sand bath, or metallic heating blocks, or the use of microwave heating.

In one embodiment of the present invention the reaction is performed either in a batch reactor or a continuous flow reactor. The synthesis based on the methods disclosed herein may be employed either in a batch reactor or a continuous flow-type reactor. The use of a flow reactor setup adds the ability achieve complete mixing of the reactants as well as in-line monitoring of the progression of the reaction. In order to at least partially overcome this limitation, a batch reactor requires intensive stirring of the reaction mixture.

In one embodiment of the reaction the elimination step is performed using a base, preferably selected from the group comprising inorganic or organic bases. In another embodiment the base is an inorganic carbonate, an inorganic hydroxide, an inorganic bicarbonate, an organic base, or a mixture thereof. In a further embodiment the base is sodium carbonate, potassium carbonate, lithium carbonate, sodium hydroxide, potassium hydroxide, lithium hydroxide, sodium bicarbonate, potassium bicarbonate, lithium bicarbonate, an organic amine, or a mixture thereof. In a specific embodiment the base is sodium bicarbonate, sodium hydroxide, sodium carbonate, triethylamine, trimethylamine, diethylamine, sodium acetate, piperidine, pyridine, or a mixture thereof, preferably triethylamine or sodium bicarbonate.

When compared to previously used methods, the catalyzed reaction produces a product mixture with an improved impurity profile, including a higher ratio of the (E) to (Z) isomers. This both simplifies the purification and improves the overall yield of the desired product. In one embodiment of the present invention the double bond present in the product is essentially in pure (E) orientation.

In one embodiment of the present invention the arylsulfonylhalide used is generated in situ effectively leading to a one-pot process for preparing the arylsulfonylpropenenitriles simplifying the overall production process.

The reaction speed is improved significantly by the addition of a catalyst; an added advantage is that the reaction also gives a higher final conversion.

The synthesis is completed by an elimination in which the previously formed halide is treated with a suitable base to produce the desired arylsulfonylpropenenitrile. The base may be an organic or inorganic base such as sodium bicarbonate, sodium hydroxide, sodium carbonate, triethylamine, trimethylamine, diethylamine, sodium acetate, piperidine, pyridine, or a mixture thereof, preferably triethylamine or sodium bicarbonate.

In one embodiment of this invention, the catalyst complex is prepared immediately before the reaction from the corresponding acid and base as the complex is highly unstable and will decompose on storage. In another embodiment of the present reaction, the catalyst complex is prepared in situ immediately before use to minimize the decomposition of the catalyst prior to the reaction.

In another embodiment of this invention the arylsulfonylhalide is prepared in situ effectively leading to a one-pot procedure for the synthesis of arylsulfonylpropylenenitriles.

In one embodiment of the invention, the desired product is isolated from the reaction mixture by crystallization using a suitable organic solvent or a suitable mixture comprising organic solvents. In another embodiment of the invention, the desired product is purified by recrystallization from a suitable organic solvent or a suitable mixture comprising organic solvents.

Experimental Section

The invention is described below with the help of examples. The examples are given only for illustrative purpose and they do not limit the scope of the invention.

EXAMPLES

Example 1: Preparation of Catalyst Complex 0.99 g (5.2 mmol) of CuI and 1.07 g (7.8 mmol) of triethylamine hydrochloride (TEA*HCl) were dissolved in 3 mL of acetonitrile at approximately 60° C. in an oil-bath to form a clear brown solution.

Example 2: Synthesis of (E)-3-tosylacrylonitrile 1.906 g (10.0 mmol) of tosyl chloride and 1.31 mL (2 eq.) of acrylonitrile was charged into the reaction vessel with 2.85 mL sulfolane; magnetic stirring was initiated and the oil bath was set to 100° C. Solution of 0.206 g (0.15 eq.) of the catalyst (CuI-TEA*HCl) to the hot reaction mixture in one portion. Reaction mixture was stirred for 3 h at 100° C. and monitored by HPLC.

Reaction mixture was cooled to room temperature, poured into 1.4 mL of triethylamine (TEA) in 20 mL purified water. The precipitate that was formed was filtered off and washed with purified water (2×5 mL) and 0.3 M HCl (2×5 mL) and the collected brownish precipitate dried. Crude yield was 1.85 g of (E)-3-tosylacrylonitrile (89%).

The crude precipitate was sonicated in 50 mL of Diethyl ether and an insoluble precipitate was filtered off. The mother liquor was concentrated in vacuo to ⅓ volume (40° C., P=650 torr) and product started to precipitate. The precipitate was filtered off and washed on filter with cold Diethyl ether (2×25 mL) and then dried on a lyophilizer. The yield of purified (E)-3-tosylacrylonitrile as white crystals was 1.13 g (54%).

The identity and purity of the product was confirmed by NMR and HPLC-MS.

The invention claimed is:

1. A process to prepare a compound of a formula (I)

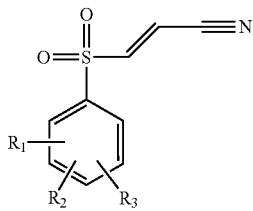

(I)

wherein $R_1$ represents a methyl group; an ethyl group, a propyl group; a butyl group; a methoxy group; an ethoxy group; a propoxy group; an iso-propoxy group; a n-butoxy group; or a tertiary butoxy group; and $R_2$ and $R_3$ represent independently a hydrogen atom; a methyl group; an ethyl group, a propyl group; a butyl group; a methoxy group; an ethoxy group; a propoxy group; an isopropoxy group; a n-butoxy group; a tertiary butoxy group; the process comprising steps of:
   i) mixing a sulfonyl halide, acrylonitrile, and a catalyst in a solvent, and
   ii) adding a base to eliminate a halide to form a desired product,
wherein the catalyst is a complex that comprises an inorganic halide and a salt of an organic compound that is prepared immediately before addition to the reaction mixture, and said solvent comprises an organic solvent.

2. The process according to claim 1, wherein, in the Formula (I):
   $R_1$ represents a methyl group in the 4-position, and
   $R_2$ and $R_3$ represent hydrogen atoms.

3. The process according to claim 1, wherein the sulfonyl halide is an iodide, a bromide, a chloride, a fluoride, or a mixture thereof.

4. The process according to claim 1, wherein the inorganic halide is a a transition metal halide.

5. The process according to claim 1, wherein the catalyst complex comprises a copper halide, the halide being iodide, bromide, fluoride, or chloride, or a mixture thereof.

6. The process according to claim 1, wherein the salt is a salt of an organic base and inorganic acid.

7. The process according to claim 1, wherein the amount of catalyst complex is less than 30 mol-% of catalyst complex relative to the amount of the sulfonyl halide.

8. The process according to claim 1, wherein the organic solvent is sulfolane, 1,4-dioxane, 2-methyltetrahydrofuran, ethyl acetate, acetone, propylene carbonate, acetonitrile, or any mixture thereof.

9. The process according to claim 1, wherein the reaction is performed at a temperature below 200° C.

10. The process according to claim 1, wherein the base used for elimination in step ii) is an inorganic base and the inorganic base is sodium bicarbonate, sodium hydroxide, sodium carbonate, or a mixture thereof.

11. The process according to claim 1, wherein the base used for elimination in step ii) is an organic based and the organic base is triethylamine, diethylamine, trimethylamine, sodium acetate, piperidine, pyridine, or a mixture thereof.

12. The process according to claim 3, wherein the sulfonyl halide is a chloride.

13. The process according to claim 1, wherein the inorganic halide is a copper halide.

14. The process according to claim 5, wherein the copper halide is iodide, chloride, or a mixture thereof.

15. The process according to claim 6, wherein the salt is a salt of an amine and an inorganic acid.

16. The process according to claim 6, wherein the salt is triethylamine hydrochloride.

17. The process according to claim 1, wherein the organic solvent is acetonitrile, sulfolane, 1,4-dioxane, or any mixture thereof.

18. The process according to claim 1, wherein the organic solvent is sulfolane.

19. The process according to claim 1, wherein the reaction is performed at a temperature below 125° C.

20. The process according to claim 11, wherein the base used for elimination in step ii) is trimethylamine or sodium bicarbonate.

* * * * *